United States Patent
Vilkomerson (10) Patent No.: US 7,902,722 B2
(45) Date of Patent: Mar. 8, 2011

(54) TRANSDUCER APPARATUS FOR INTRAVASCULAR BLOOD FLOW MEASUREMENT

(75) Inventor: David Vilkomerson, Princeton, NJ (US)

(73) Assignee: DVX, LLC, Princeton, NJ (US)

( * ) Notice: Subject to any disclaimer, the term of this patent is extended or adjusted under 35 U.S.C. 154(b) by 166 days.

(21) Appl. No.: 12/384,412

(22) Filed: Apr. 3, 2009

(65) Prior Publication Data
US 2009/0251028 A1 Oct. 8, 2009

Related U.S. Application Data

(60) Provisional application No. 61/123,091, filed on Apr. 3, 2008.

(51) Int. Cl.
  *H04R 17/00* (2006.01)
  *H01L 41/08* (2006.01)
  *A61B 8/14* (2006.01)

(52) U.S. Cl. ......... 310/322; 310/334; 310/366; 310/367; 29/25.35; 600/454

(58) Field of Classification Search .................. 310/322, 310/334, 365, 367, 369; 600/454; 29/25.35
See application file for complete search history.

(56) References Cited

U.S. PATENT DOCUMENTS

| 3,798,474 A | * | 3/1974 | Cassand et al. ............... 310/331 |
| 4,918,666 A | * | 4/1990 | Beauducel et al. ............. 367/15 |
| 2004/0101150 A1 | * | 5/2004 | Hooley et al. ................. 381/190 |
| 2004/0135475 A1 | * | 7/2004 | Omata et al. .................. 310/367 |

FOREIGN PATENT DOCUMENTS

JP 56-131221 A * 10/1981

* cited by examiner

*Primary Examiner* — Thomas M Dougherty
(74) *Attorney, Agent, or Firm* — Plevy & Keene LLP (57) ABSTRACT

A dual spiral transducer and method of manufacture of same is disclosed. In one aspect, the transducer comprises a central rod, a first spiral piezoelectric electrode wrapped around a circumference of the rod, the electrode being advanced around the rod at a determined angle determined based on a length of a single complete turn around the rod and a diameter of the rod and a second spiral piezoelectric electrode wrapped around the circumference of the rod, the second spiral electrode being electrically isolated, and offset, from the first spiral electrode by a known distance. A second set of spiral electrodes can be integrated into the structure so that both transmission and reception of signals is feasible.

27 Claims, 4 Drawing Sheets

Fourier Transform

FIG. 11B

TRANSDUCER APPARATUS FOR INTRAVASCULAR BLOOD FLOW MEASUREMENT

CLAIM OF PRIORITY

This application is a non-provisional of U.S. Patent Application No. 61/123,091 filed Apr. 3, 2008, hereby incorporated in its entirety by reference into this application.

FIELD OF INVENTION

This invention relates to the field of transducers and more particularly to transducer apparatus and methods that can be introduced into blood vessels for measuring blood flow within them.

BACKGROUND OF INVENTION

The related U.S. patent, Transducer Apparatus and Method for Intravascular Blood Flow Measurement", assigned to the same assignee as the present invention, discusses the importance of measuring blood flow in a non-invasive manner. As disclosed tissue viability depends upon adequate blood flow in the feeding vessels. Doppler ultrasound is widely used for such measurement, and is well understood; see, for example, "Doppler Ultrasound", by Evans and McDicken, as is disclosed in the aforementioned related patent application.

As described in the aforementioned related patent application, minimally-invasively placing Doppler transducers within the blood vessels, e.g. by means of catheters, is desirable. The diffraction-grating transducer described in the referenced application provides apparatus and methods to accomplish such measurement. In the referenced disclosure, diffraction grating ultrasonic transducers are used to produce beams of ultrasound that are backscattered by moving blood so that Doppler measurement methods may be used to calculate the blood velocity, and thus determine blood flow.

In order to spread their beams over the area of the blood vessel, the transducers, taught in the aforementioned related patent application, depend upon their narrow width to cause diffraction. As the amount of ultrasound scattered by blood is inversely proportional to wavelength, small wavelength (high frequency) is desirable for low power requirements. Thus, those transducers can only be a few, e.g. 2 or less, wavelengths wide. This limitation restricts the devices disclosed therein to being one or more long extended ribbon-like transducers.

When using plastic piezoelectrics, as described in the aforementioned related patent application, unless the transducers are quite long, or multiple transducers are used, the impedance levels of the transducers make matching to the sending and receiving electronics, as is well known a requirement for efficient transmitting and reception, difficult.

Moreover, these transducers must be patterned, i.e. have alternately reversed polarity sections, in order to form the diffraction-grating transducer, of the spacing corresponding, for example, to two acoustic wavelengths. For example, a repeating pattern of 150 microns is required for 20 MHz ultrasound. While not in any way straining the capability of photolithographic art, such patterning in metal requires masking and other procedures that may make fabrication of these transducers not inexpensive.

SUMMARY OF INVENTION

Figure 3:
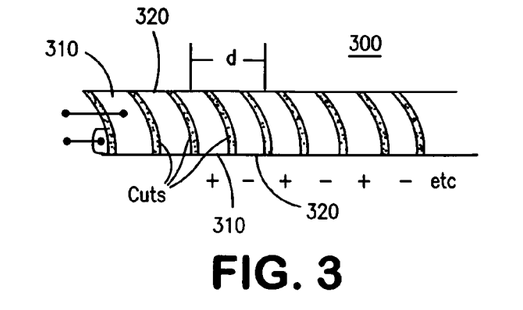
FIG. 3 illustrates a helical diffraction-grating transducer (H-DGT); the windings are shown at a relatively low angle to the axis for clarity.

An improved diffraction-grating transducer structure providing intravascular blood flow measurement capability is disclosed. The transducer structure comprises two or more electrodes helically "wound" around a central core, as shown in FIG. 3. The spacing between the electrodes is dependent upon a desired frequency of operation, e.g. 150 microns for 20 MHz operation. Connection to these multiple helices that form the transducer may easily be affected at either end of the structure, an advantage over the need to bring "fingers" to each electrode as previously taught. Further, the helical diffraction gratings, so formed, are symmetric around the axis; the beams produced by gratings are similarly symmetric, i.e. the wavefronts produced by the grating structure are cone-like, expanding to fill the vessel. These wavefronts, rather than depending upon the narrowness of the transducer, as in the previously taught configuration, insonate the entire vessel. A further advantage of the new structure is that the helical windings forming the diffraction-grating-transducers (DGT) carry current and produce a magnetic fields, i.e. they act as electrically inductive coils The inductance of these coils can designed to balance out the capacitance inherent in the piezo-electric transducer elements, "series resonant", making the transducer have substantially pure real impedance and be low enough impedance to be "matched", for an improved power transfer to the sending and receiving electronics.

In another aspect of the invention, a single structure can hold both the transmit and receive portions of a transducer system.

In still another aspect of the invention, a cylindrical wavefront can be launched by the helical diffraction-grating transducer and be utilized for pulse-echo measurement of the diameter of the vessel, allowing quantitation of volume flow.

These and other aspects and advantages of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 11(*a*) illustrates the spatial structure of the transmitting windings of the quad H-DGT of FIG. 8 and the associated Fourier transform;

FIG. 11(*b*) is the spatial structure and Fourier transform of the receiving windings.

DETAILED DESCRIPTION OF THE INVENTION

Figure 1A:
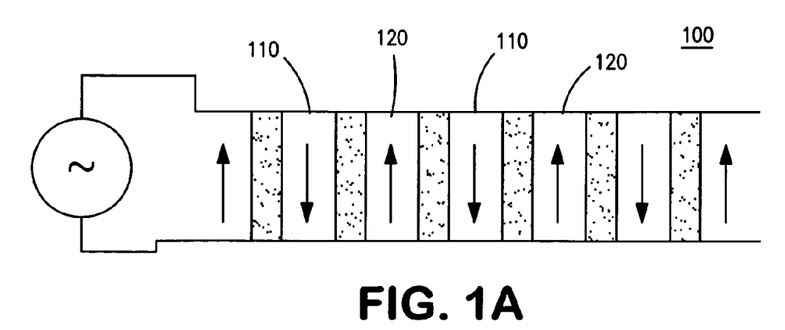
FIG. 1a shows a conventional double-beam diffraction-grating transducers with alternating polarized transducer elements
Figure 1B:
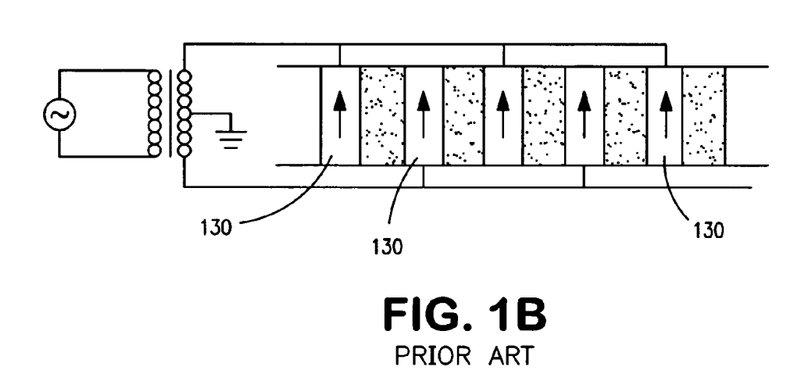
FIG. 1b shows a conventional double-beam diffraction grating transducer with non-alternating polarized transducers.

FIGS. 1*a* and 1*b*, which are disclosed in the aforementioned related patent application, describe the structure of thin, flexible transducers taught for intravascular Doppler flow measurement. The transducer 100 is represented as a double-beam diffraction-grating transducer (DGT) composed of alternating-polarized piezoelectric elements 110, 120 between two sheet electrodes (FIG. 1*a*) and alternately driven elements (FIG. 1*b*). These structures produce alternating positive and negative motion, resulting in two beams, as taught in detail in the aforementioned related patent application.

However, in the aforementioned related patent application the emphasis is on the alternate reversed-poled structure, as the connections required for the alternate driven element configuration are difficult in the "ribbon" transducers.

Figure 2:
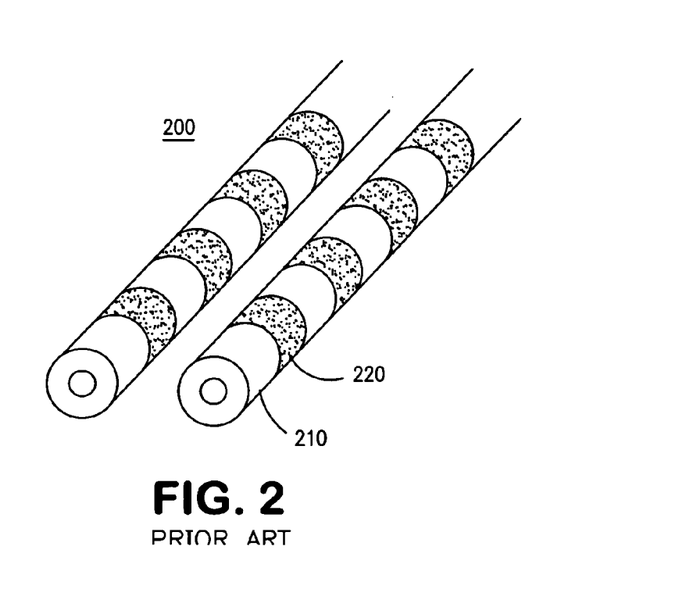
FIG. 2 shows a conventional diffraction-grating transducer consisting of cylindrical sections.

While the aforementioned related patent application is directed to very narrow flat versions similar in structure to striplines, FIG. 10 (reproduced herein as FIG. 2) teaches using cylindrical transducers, to gain the advantage of cylindrical wavefronts. While such a structure produces cylindrical wavefronts that fill a blood vessel, the production of such a structure is difficult. In this case, the piezoelectric elements 210 of each polarization must be connected together for poling without contact with the piezoelements 220 that will be poled in the opposite direction. In addition, as separation of the elements is typically a few tens of microns, such fine detail over a long structure is difficult to achieve. Moreover, the requirement for delivering the high voltage for poling each of the elements uses up valuable space on the transducer and, thus, reducing an active area of the transducer (i.e., the area above the conductive element).

FIG. 3 shows a side view of an exemplary embodiment of a transducer structure 300 in accordance with the principles of the invention to produce cylindrical waves. In this exemplary embodiment of the invention, two continuous electrodes 310, 320 are "wrapped" around a rod. While FIG. 3 shows the electrodes (conductive bands) at an approximately 80-degree angle to the axis of the rod carrying them, for ease of visualization, the angle of the electrodes to the rod axis for helical DGT operating in the range useful for intravascular blood flow measurement is generally closer to 90-degrees. As described in the aforementioned related patent application, the distance (d) between similarly poled areas is a few ultrasound wavelengths. Thus, the angle at which the ultrasound beams are launched, θ, is determined as:

$$\theta = \sin^{-1}(\lambda/d) \quad (1)$$

where
θ is the launch angle of the beam to the rod axis,
λ the wavelength of the ultrasound being used, and
d is the center-to-center distance between equally poled regions.

For example, to launch a 45° beam using 30 MHz ultrasound (i.e., a 50 micron wavelength) requires a distance "d" of 1.414λ (sin 45°=1/1.414). Hence, the distance or pitch "d" of FIG. 3 would be 1.414×50 microns, or 71 microns, in this specific case.

The angle of the electrode to the axis of the rod, for this example, must be such that when "wound" once around the circumference of the rod (i.e., pitch "d" FIG. 3), the electrode position must advance by 71 microns. To achieve the desired distance, the angle of the electrode to the rod axis, φ, is determined as:

$$\phi = \cos^{-1}(d/\pi D) \quad (2)$$

where D is the diameter of rod.

Thus, if the core of the transducer is a 2 mm (6 French) catheter, the angle may be determined as:

$$\phi = \cos^{-1}(0.071/2*\pi) = 89.4° \quad (3)$$

Therefore, the wavefronts produced by this helical DGT can be well approximated by assuming the windings are actually perpendicular to the rod, and Doppler signals resulting from a blood cell moving parallel to the rod differ from a conventional DGT Doppler signal by less than one percent by $(1-\cos 89.4°/1) = 5 \times 10^{-6}$), because of the slight angle of the electrodes to the rod axis.

A particularly easy way to fabricate the desired helical electrodes is to form them by cutting a screw-thread-like pattern into a metal layer deposited on an insulating rod of the desired size. The cut removes a portion of the metal, e.g. 15 microns wide. Such a cut can be made like a screw thread, i.e. by rotating the rod (core) of the structure beneath a cutter while the cutter slowly advances parallel to the axis. For the 30 MHz example referred to above, the cutter would advance by 71 microns with every rotation of the rod to make one cut the entire length of the rod; this cut would be repeated from the original end but with the cutter starting point advanced 35.5 microns (i.e., one-half the distance between adjacent windings of the first spiral winding or screw-thread like pattern) further along the rod than the previous cut; when completed, a second electrode, electrically isolated from the first, would be formed, with both electrodes spatially repeating every 71 microns, and separated by 20.5 microns (i.e., 35.5–15 microns). Thus the structure of FIG. 3 would be made (at the angle of 89.4° rather than the approximately 10° shown in FIG. 3) using well-known screw cutting methods.

For the very narrow cuts required by using high ultrasound frequencies, a focused laser beam may be used for cutting. It should be noted, however, optical diffraction gratings are made using mechanical means (e.g., a diamond point) with typical cuts of a few tenths of a micron width with a spacing of only a micron or two, so the structures described here could be made mechanically. In another aspect of the invention, the windings may be composed of wires that wound around a turning central rod. The wires may be held at a desired angle with respect to the central rod to achieve the desired single turn length (d) described with regard to equation 1.

After the two electrodes have been formed, they can be coated with a piezoelectric material of an appropriate thickness for the desired frequency of operation, e.g. for resonance, λ/4, where λ is the acoustic wavelength in the piezoelectric material, as is well-known to those skilled in the art. If the piezoelectric material used requires separation between elements because of strong lateral coupling (i.e. lateral waves influence surrounding elements, as for piezoceramics), the material may be cut similar to the base material, with two screw thread-like cuts. Piezoplastic materials, e.g. P(VDF-TrFe), which are particularly desirable for intravascular use because of their biocompatibility and lightness, do not need such cuts as they do not support lateral coupling (as is well-known in the art). These layers can be applied by dip-coating the rod with the properly prepared liquid precursor of the copolymer material.

Following the deposition of the piezoelectric material, a ground electrode may be deposited, e.g. sputtered, over an active area. The two electrodes are then used to polarize the material above them (active region). As was previously taught in the referenced earlier patent, the material can be polarized in alternating directions so that if both electrodes are driven together a double beam is produced. This is achieved by applying a polarizing voltage to one of the windings through an electrical contact means with the outer conductive coat grounded. The material above the second winding is then polarized in the opposite direction by connecting it to a voltage of opposite polarity but with a same magnitude while holding the outer layer at ground. If the electrodes will be driven in opposite polarities, for example to cancel out their magnetic fields, as will be discussed later, both electrodes will polarize the material in the same direction by not reversing the direction of poling.

For example a copolymer piezoplastic P(VDF-TrFe) requires a voltage of 60 V/micron to polarize it. For the 30 MHz example considered above, a λ/4 layer would be 18 microns thick, requiring approximately 1080 V to polarize it.

Note that the only connection required would be one end of the rod, as the electrodes are continuous, and therefore there is no need for the structures to bring the voltage to each element.

If the windings are alternately polarized, the two windings can be connected together and a voltage applied between the outer shell electrode and the two electrodes will cause alternate piezoelectric elements to move in opposite directions; thus, launching two beams at an angle θ of $\pm\sin^{-1}(\lambda/d)$. The geometry for determining the angle θ is illustrated in U.S. patent application Ser. No. 10/953,276, entitled Vessel Flow Monitoring System and Method, filed on Sep. 29, 2004, the contents of which are incorporated by reference herein.

Figure 4:
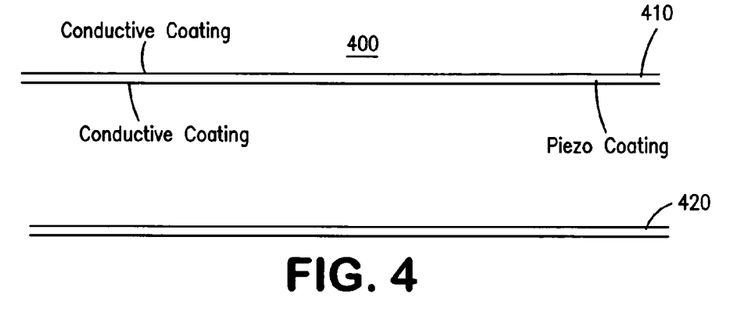
FIG. 4 is a schematic representation of a cylindrical receiving element that can be used with an H-DGT to measure fluid flow by means of Doppler.

A second rod (or tube) with a uniform coating of piezoplastic of the same λ/4 thickness, and therefore the same resonant frequency, can be used as a receiver. FIG. 4 illustrates a structure wherein two surfaces 410, 420 of a rod or tube are substantially parallel. As is well known to transducer designers, such a structure would receive beams perpendicular to its axis.

Figure 5:
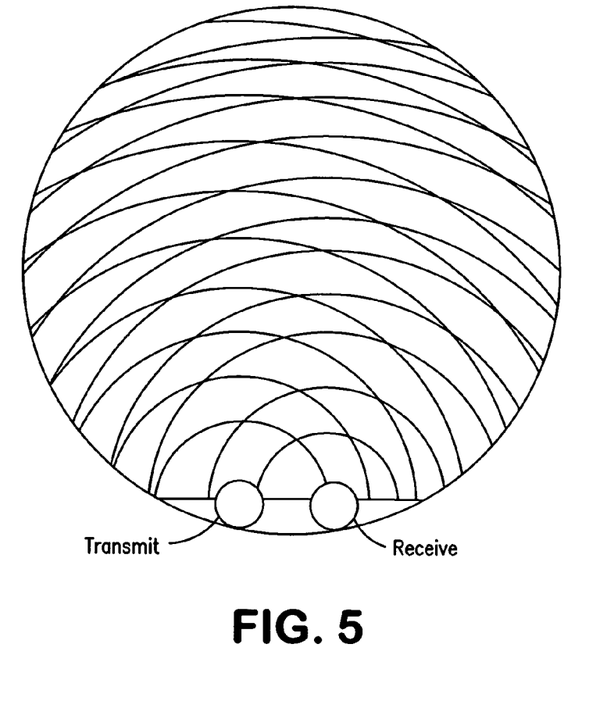
FIG. 5 is a schematic representation of the overlap between the wavefronts of a transmit H-DGT and a cylindrical receiver shown in FIG. 4.

FIG. 5 shows a configuration 500 of how the transmitted beams from the structure of FIG. 3 and the receiving beam produced by the transducer of FIG. 4 fill and overlap over a typical blood vessel. Cone-shaped transmitted wavefronts are produced without regard to the diameter of the transmitting helical DGT.

Figure 6:
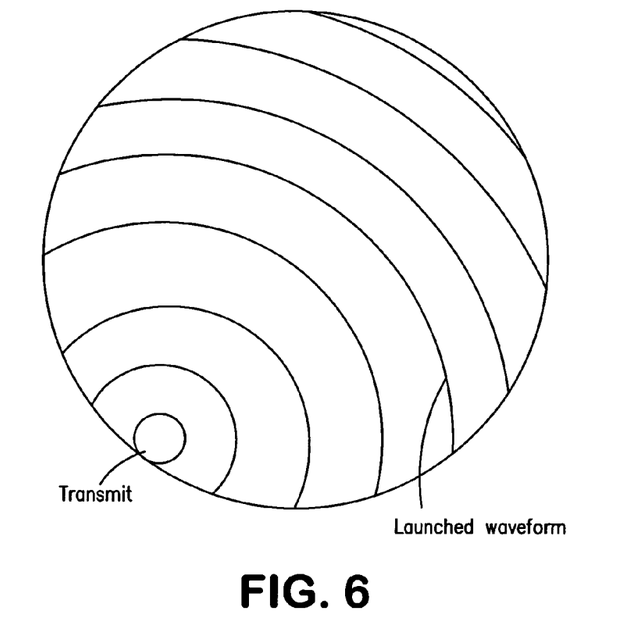
FIG. 6 illustrates the use of the structure shown in FIG. 4 to determine the diameter of a vessel.

A further advantage of the cylindrical wavefronts produced by the structure of FIG. 4 is that they may be used to measure the diameter of the vessel in which it is placed. FIG. 6 illustrates an example of the measurement of a diameter of a blood vessel using a reflected waveform. In this case, the reflected wave directly from a cell wall is exactly opposite the transducer. Therefore the diameter of the vessel can be measured by the usual pulse-echo method. In one aspect, the transducer is, as shown, lying on the wall of the vessel, provides an accurate measurement of the blood vessel diameter. That situation is the usual mechanically stable orientation of guide wires or catheters, but, if necessary, it can be assured by, for example, using the shape of the structure to generate forces from the flowing blood to push it to the vessel wall, or by using fins to do so. See, for example, WO/2000/013736 "Fin Tipped Flow-guided Catheter," Rottenberg and Shoshani, the contents of which are incorporated by reference, herein, which discloses shaping the structure to generate such forces.

One of the considerations for designing the intravascular transducers in the related aforementioned previous patent application was the need to achieve impedance levels that matched signals line impedance levels, e.g. 50 ohm. In that application, we described there, for example, the strategy of driving for example, 6 transducers in parallel to reduce the impedance to levels commensurate to stripline signal lines, in the range of 20 to 200 ohms.

Figure 7:
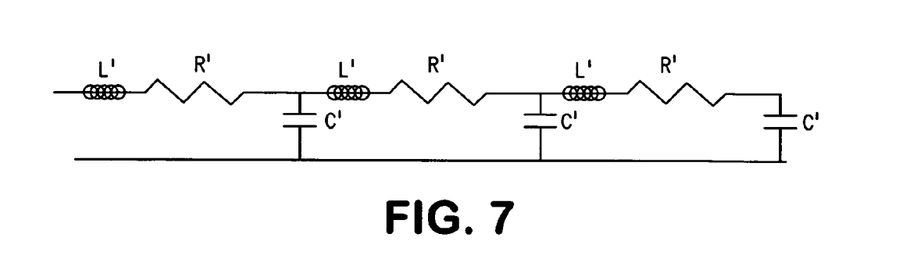
FIG. 7 is the circuit model applicable to a winding of an H-DGT.

The helical structure of these disclosed transducers provides for integrated "matching coils" in these transducers. The combination of the coiled structure of the helical electrodes with the capacitance associated with the piezoelectric layer of the transducers can be modeled by the structure shown in FIG. 7. The impedance of the (inductive) helical structure is opposite in sign to the (capacitive) impedance of the transducer structures. The resistive component is determined by the thickness of the metal layer that forms the electrode helices over the total length of the electrode, which is proportional to the product of the number of turns and the radius, and the "radiative resistance" that corresponds to the energy transmitted out of the structure. As is well-known, the total inductance is proportional to the number of turns squared times the area of the helical coil and the permeability of the core, and inversely proportional to the length. That is, $$L=N^2 A\rho/Nd \qquad (4)$$

where

L is the inductance

N is the number of turns

A is the area of the coil

ρ is the permeability of the core and d is the spacing between turns.

The total capacitance is proportional to the area of the piezoelectric transducers, the relative dielectric coefficient, and inversely proportional to the thickness of the piezoelectric layer.

$$C=kA_p\epsilon/T \qquad (5)$$

where k is a constant of proportionality $A_p$ is the area of the transducer $\epsilon$ is the dielectric constant; and T is thickness of the piezoelectric layer.

It should be noted that when the two electrodes are driven together from one end, as is possible with reverse poling, the mutual coupling of the two helical coils is so high that the impedance of the two in parallel is about the same as driving one individually. That is, the currents in the two electrodes, and the magnetic field produced by them, is the same, so the magnetic energy in the field is the same if one is driven as both. As the inductance is a measure of magnetic energy, it follows that the inductance of both windings is almost exactly the same as one. If the coils are driven from opposite ends, for example one coil from the left end of FIG. 8 and the other from the right, as is possible with this structure, the currents in the two coils will be in the opposite direction, so the magnetic fields they produce will almost cancel; therefore, by the same discussion as above, the total inductance seen when driving both coils, but from opposite ends of the structure rather than the same end, is typically 10% of the value of a single coil or both coils when driven together from the same end of the structure.

In addition to adjusting the inductance by the manner of connection to the spiral coiled windings, the inductance can also be adjusted by altering the permeability of the core, (i.e., ρ of Equation 4). For example, a ferrite powder rod rather than a ceramic rod would increase the inductance of each coil by orders of magnitude. The ability to adjust the inductance, by altering the driving means as described in the last paragraph, or by altering the magnetic permeability of the core, provides important design freedom for these transducer structures, thereby allowing excellent impedance matching to these structures which in the past has been difficult, particularly for piezoplastics.

Figure 8:
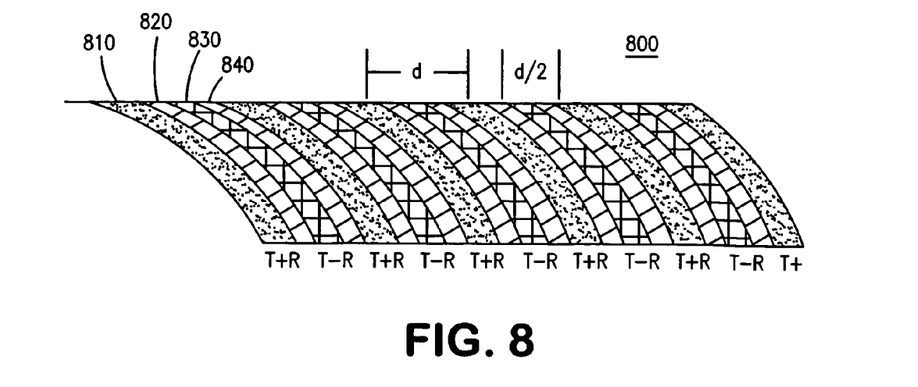
FIG. 8 shows the structure of a quad H-DGT, showing the alternatively driven transmit windings, T+ and T−, and the uniformly polarized receive elements, R.

In addition to separate transmit and receive transducers, it is possible to combine the two functions in one H-DGT. In another aspect of the invention, as shown in FIG. 8, four helical electrodes can be used, 810-840. Two of the electrodes are for the transmit DGT; these electrodes are labeled T+ for the electrode driving material polarized with positive voltage on the outer electrode, and the other helical electrode T− for negative voltage polarization, as previously explained. These electrodes can be driven together, in the alternately poled configuration of FIG. 1(*a*). (If alternate polarization was not desirable, they could be polarized in the same direction and driven in opposite phases, by using a center-tapped transformer, as shown in FIG. 1(*b*), for example). The spatial period distance between the (T+) winding is "d," which sets the beam angle, as noted in equation (1), and the distance between the two receive helical electrodes of the same width and spacing shown in FIG. 8, labeled "R," is therefore "d/2." The other transmit electrode, (T−) is between the two R electrodes, and also has a spatial period of d. Note that all of the windings can be connected from one or the other end of the structure, making it easy to connect to these electrodes.

Figure 9:
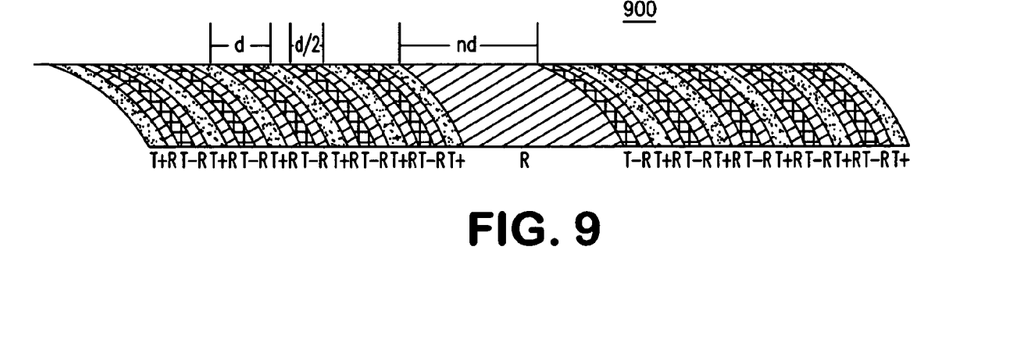
FIG. 9 portrays the mixed-mode H-DGT, where the receive elements are widened to provide distinct receiving areas.

The two "R" electrodes provide receiver elements on the same rod as the transmitter. One way of providing this capability is shown in FIG. 9, where the receiver electrodes separated by 3 mm are widened from the usual 20 microns to 1000 microns (1 mm) wide.

Figure 10:
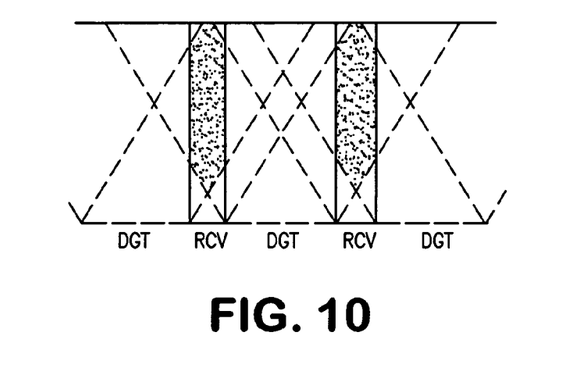
FIG. 10 illustrates the receiving pattern of the structure shown in FIG. 9.

As shown in FIG. 10, the region in which the receive beams from the widened R electrodes and the transmitted beams produced by the T+ and T− electrodes would provide overlapping coverage of the vessel lumen from 0.8 to 5.2 mm from the receiver surface (assuming a 30° beam). The dimensions of the receiver and transmitting portions of the transducer system, i.e. how often and how wide the receiver electrodes are widened and the "pitch" (spacing) of the T+ and T− electrodes can be adjusted for the particular dimensions of the vessel in which the structure would be used. For example, if the diameter of the vessel is only 3 mm, the length of the transmitting portion of the rod would be reduced to less than 3/co tan(30°), so that the transmitting beam energy would not be wasted insonating volume outside the receiving section.

As the four helical electrodes 810-840 are magnetically coupled, i.e. their magnetic fields overlap, the manner in which the transmitting helices are driven, i.e. current in one direction or the other, will affect the best manner the receiving helices should be connected. For example, if the transmitting coils are driven from the same end, in the alternating polarized configuration, one receiving electrodes should be connected at one end of the structure and the other at the other end; the voltage induced from the transmitting helices will be in opposite direction in the two receiving electrodes, "bucking out" voltage induced by the transmitting electrodes. One skilled in the art will recognize there are other configurations, depending upon whether alternating polarization, as discussed, is used, or non-alternating polarization, and driving from different ends, that accomplish the same thing; what is key is recognizing that the area within the helical DGT will contain the magnetic field produced by the electrodes, and the magnetic vector will depend on the direction of current, allowing cancellation or addition of induced voltages.

Another configuration using four helical windings of FIG. 8 uses uniform receiver electrodes, connected together, of the same dimensions as the transmitting electrodes. In this configuration, the piezoelectric material for both "R" receiving electrode helices is poled in the same direction. As FIG. 8 shows, the spatial period of the receiving helices is "d/2" where the spatial period of the alternately poled transmitting helices is "d". Referring to Equation 1, if the frequency of operation is such that $\lambda/d$ is >0.5, corresponding to transmitting a beam at θ= or >45°, the half spatial period of the receive helices corresponds to an angle of θ whose sine is $\lambda/(d/2)$, i.e. >1. As the maximum value for real values of sine θ is 1, the receive electrodes cannot launch or receive beams at this angle. Therefore the only beam angle the R electrodes can receive is perpendicular to the axis of the rod.

Figure 11A:
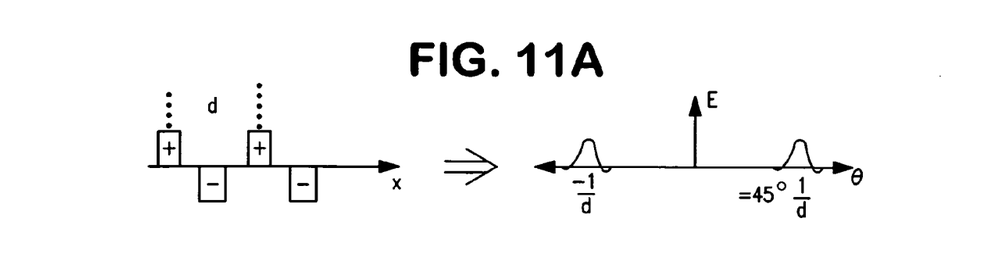
Figure 11B:
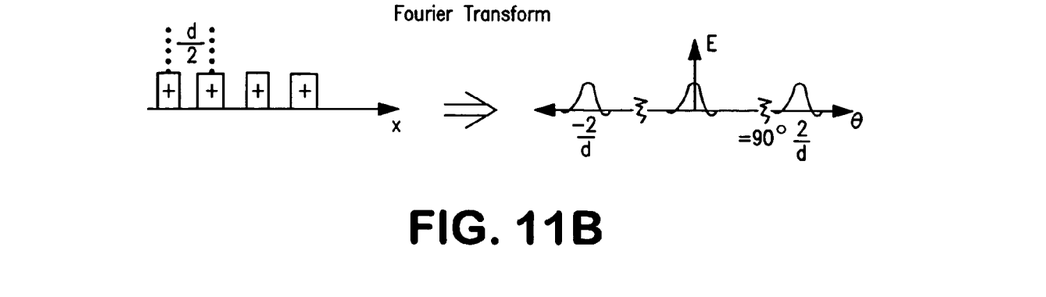

This is further clarified by remembering, as is known to those skilled in the art, that the beams launched into the far field correspond to the Fourier transform of the illumination on the aperture. As shown in FIG. 11, the oppositely poled transmit helices will have no zero-frequency (0-frequency) component and have a major Fourier component at 1/d in Fourier space; the receive electrodes, being poled the same direction, have a spatial period half that of the transmit electrodes, so the corresponding Fourier component is twice that of the transmit electrode far-field pattern. If the transmit angle is 45° or greater, the double angle is 90° or greater, i.e. an evanescent wave. There is a 0-frequency component, corresponding to a beam perpendicular to the axis. Therefore, the R electrodes will receive the Doppler shifted frequencies arising from blood cells traversing the angled beams from the transmitting electrode helices. In this way the receiver electrodes are completely integrated into the transducer configuration. (These receive electrodes can also be used to measure the vessel diameter in the same manner as the cylindrical transducers described above, as they produce perpendicular cylindrical waves like those transducers.)

The relation between spatial period and launched waves as described by the Fourier Transform is well-known to those skilled in the art; see "Higher Order Diffraction Grating Transducers", Vilkomerson, et al, Proc. of Medical Imaging 1997, SPIE Vol. 3037, pp 206-212, for other illustrative examples showing this relationship.

As an example of such a four-helice electrode transducer, consider the previously referenced 30 MHz helical DGT. To launch or transmit a beam at approximately 45°, the spatial period "d" is preferable in the order of $1.414\lambda = 70.7$ microns. With a 7.7 micron kerf (the spacing between each electrode) each helical electrode would be approximately 10 microns wide. (Four times the electrode width of 10 microns plus four times the kerf width of 7.7 microns provides the spatial period of 70.8 microns). Using conventional formulae for calculating the inductance, capacitance, and resistance, with half-mil thick copper cut as described to form four helical electrodes on a rod of magnetic permeability 1 and of 1.4 mm in diameter, a structure 17 mm long would have an impedance at 30 MHz of approximately 40 ohms. This is an impedance level that can be easily matched using either stripline or miniature coax. The transmitting windings would produce beams filling the vessel with wavefronts traveling at 45°, and the receiving windings intercepting the backscattered and Doppler-shifted ultrasound so that the velocity of the blood may be measured. Using the receive electrodes, the diameter could also be measured, and from the velocity and area of the vessel the flow could be calculated.

Thus the H-DGT provides advantages for making intravascular blood-flow measuring systems of small size, desired beam shapes, vessel-diameter measurement, and low cost of fabrication.

In another aspect of the invention, a first spiral groove may be etched into an insulating (or non-electrically conductive) rod. The first spiral groove may be formed in accordance with the previously described equations 1-5. A metallic element may be deposited in the first spiral groove. The width and depth of the groove may be determined based on a desired electrical characteristic of the deposited metallic element. A second spiral groove may further be formed within the insulating rod, offset and parallel to the first spiral groove. A metallic element may be deposited within the second spiral groove. The metallic elements within the first and second spiral grooves are electrically isolated from each other.

In one aspect, the insulating rod may be coated with a non-electrical material within which first and second grooves are formed. After depositing the metallic element in each of the first and second spiral grooves, the remaining (i.e., non-grooved) non-electrical material may be removed, to leave electrically isolated first and second metallic elements within respective first and second grooves wound around the insulating rod.

While there has been shown, described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A transducer comprising:
   a central rod having a conductive layer deposited thereon;
   a first spiral groove of a determined pitch extending laterally in said conductive layer along said rod, said pitch being determined based on an operating frequency of said transducer and a launch angle of a transmitted beam;
   a second spiral groove extending laterally in said conductive layer along said rod, said second spiral groove having a pitch substantially similar to that of said first spiral groove and being offset from said first spiral groove by a known distance, wherein a first set of electrically isolated first and second conductive bands are formed between said first and second spiral grooves;
   a piezoelectric material of a known thickness deposited on at least said first and second conductive bands for generating an acoustic wave; said thickness being determined based on a desired frequency of operation, said piezoelectric material on said conductive bands forming a first set of first and second electrodes; and
   a conductive layer deposited on top of said piezoelectric material forming a conductive electrode with respect to each of said first and second electrodes, wherein an impedance of said transducer is based on at least one of: an inductance component dependent upon a permeability of said central rod, a capacitance of said transducer and an application of a voltage to each of said conductive bands.

2. The transducer of claim 1, wherein an angle of said first spiral groove with respect to a longitudinal axis of said central rod is determined as:

$$\phi = \cos^{-1}(d/\pi D)$$

where D is the diameter of the rod and d is said pitch.

3. The transducer of claim 1 wherein said piezoelectric material is a P(VDF-TrFe) compound.

4. The transducer of claim 1, further comprising:
   means for applying a first voltage to a first one of said first and second electrodes and corresponding conductive electrode; and
   means for applying a second voltage to a second one of said first and second electrodes and corresponding conductive electrode.

5. The transducer of claim 4, wherein second voltage is of a polarity opposite that of said first voltage.

6. The transducer of claim 4, wherein said first voltage is applied to said electrode at a first end of said rod; and
   said second voltage is applied to said electrode at a second end of said rod.

7. The transducer of claim 4, wherein said first and second ends are a same end of said rod.

8. The transducer of claim 1, wherein said piezoelectric material has a thickness of at least one-quarter a wavelength of the operating frequency.

9. The transducer of claim 1 comprising:
   a second set of electrodes substantially similar to said electrodes in said first set of electrodes and, electrically isolated from each other and from said electrodes in said first set of electrodes said second set of electrodes being positioned adjacent to said first set of electrodes, said second set of electrodes operating as a receiving unit.

10. The transducer of claim 1, said impedance is adjusted by balancing said inductance component against a capacitive component.

11. A transducer comprising:
    a central rod;
    a first piezoelectric element spirally wrapped about said central rod at a determined pitch extending laterally along said rod, said pitch being determined based on an operating frequency of said transducer and a launch angle of a transmitted beam;
    a second piezoelectric element spirally wrapped about said central rod electrically isolated from and substantially parallel to said first piezoelectric element; and
    a contact attached to each of said first and second piezoelectric elements, said contact providing a voltage to a corresponding one of said first and second piezoelectric elements, with respect to a ground electrode, wherein an inductance of said transducer is dependent upon at least one of: a permeability a material of said core and application of a voltage to corresponding contacts.

12. The transducer of claim 11, wherein an angle of said first piezoelectric element with respect to a longitudinal axis of said rod is determined as:

$$\phi = \cos^{-1}(d/\pi D)$$

where D is the diameter of the rod and d refers to said pitch.

13. The transducer of claim 11 wherein said piezoelectric element is a P(VDF-TrFe) compound.

14. The transducer of claim 11 wherein said ground electrode is deposited on at least each of said piezoelectric elements.

15. The transducer of claim 11, wherein voltage applied to said second piezoelectric element is of a polarity opposite that of a voltage applied to said first piezoelectric element.

16. The transducer of claim 11, wherein said contacts are positioned at opposite ends of said rod.

17. The transducer of claim 11, wherein said contacts are positioned at a same end of said rod.

18. The transducer of claim 11, wherein each of said piezoelectric elements have a piezoelectric material having a thickness of at least one-quarter wavelength of the operating frequency.

19. The transducer of claim 11, wherein an impedance of said transducer is determined by balancing said inductive component with a capacitive component of said transducer.

20. The transducer of claim 11, wherein said inductance is determined as:

$$L = N^2 A \rho / Nd$$

where
L is the inductance
N is the number of turns
A is the area of the coil
$\rho$ is the permeability of the core and
d is the spacing between turns (pitch).

21. The transducer of claim 19, wherein said capacitive component is determined as:

$$C = k A_p \epsilon / T$$

where
k is a constant of proportionality
$A_p$ is the area of the transducer
$\epsilon$ is the dielectric constant; and
T is thickness of the piezoelectric layer.

22. A method for fabricating a spiral transducer, comprising:
depositing a metal layer on a central rod having a desired permeability;
removing a first and a second section of said metal layer of a known width in a spiral matter along said central rod, said first section having a pitch with respect to a longitudinal axis of said central rod based on an operating frequency of said transducer and a launch angle of a transmitted beam and said second section being substantially parallel to said first section, said first and second sections forming electrically isolated first and second conductive bands therebetween;
depositing a piezoelectric element on said first and second conductive bands;
depositing a conductive layer on each of said piezoelectric elements associated with said first and second conductive bands, said conductive layer forming an electrode element and a part thereof forming an electrical contact thereto;
forming a first contact at a first end of said rod in contact with said first conductive band;
forming a second contact at second end of said rod in contact with said second conductive band.

23. The method of claim 22, wherein said first and second ends are the same end of said rod.

24. The method of claim 23, wherein said first and second ends are opposite ends of said rod.

25. The method of claim 23, wherein an inductance of said transducer is determined as:

$$L = N^2 A \rho / Nd$$

where
L is the inductance
N is the number of turns
A is the area of the coil
$\rho$ is the permeability of the core and
d is the spacing between turns (pitch).

26. The transducer of claim 4, wherein said piezoelectric elements associated with corresponding first and second electrodes is poled in opposite directions so the same voltage can be applied to both electrodes.

27. The transducer of claim 1, wherein said conductive electrodes associated with said first set of first and second electrodes are electrically connected together.

* * * * *